(12) United States Patent
Tsai et al.

(10) Patent No.: US 8,777,411 B2
(45) Date of Patent: Jul. 15, 2014

(54) FUNDUS EXAMINATION DEVICE CAPABLE OF AIDING IN GAZE FIXATION AND IMAGE FOCUSING

(71) Applicant: Crystalvue Medical Corporation, Taoyuan County (TW)

(72) Inventors: Che Liang Tsai, Taichung (TW); Chung Ping Chuang, Taoyuan (TW); Yen Jen Chang, Kaohsiung (TW)

(73) Assignee: Crystalvue Medical Corporation, Taoyuan County (TW)

( * ) Notice: Subject to any disclaimer, the term of this patent is extended or adjusted under 35 U.S.C. 154(b) by 0 days.

(21) Appl. No.: 13/728,645

(22) Filed: Dec. 27, 2012

(65) Prior Publication Data

US 2013/0286346 A1 Oct. 31, 2013

(30) Foreign Application Priority Data

Apr. 27, 2012 (TW) .............................. 101115068 A

(51) Int. Cl.
*A61B 3/14* (2006.01)
*A61B 3/10* (2006.01)
(52) U.S. Cl.
USPC .......................................... 351/206; 351/211

(58) Field of Classification Search
USPC .................................................. 351/200–246
See application file for complete search history.

(56) References Cited

U.S. PATENT DOCUMENTS 6,220,706 B1 * 4/2001 Foley ............................ 351/209
8,488,895 B2 * 7/2013 Muller et al. ................. 382/254

\* cited by examiner

*Primary Examiner* — Mohammed Hasan
(74) *Attorney, Agent, or Firm* — Rabin & Berdo, P.C.

(57) ABSTRACT

A fundus examination device aiding in gaze fixation and image focusing includes a light projecting device for projecting an examination light to illuminate an examinee's fundus; an illuminating system for transmitting the examination light to the examinee's eye and receiving a fundus image; an imaging system for showing the fundus image; and a focusing and gaze-fixation device located in the illuminating system and including a focus mask formed in a focusing zone, on which the examinee's eye focuses. The focus mask includes a split image screen surrounded by a light-penetrable structure, and gaze fixation devices for forming gaze-fixation images at examinee's eye focusing positions within the focusing zone, such that the split image screen and the gaze-fixation images are located at different focal positions corresponding to the examinee's eye curvature. Therefore, when a split image focusing is completed, the gaze-fixation images are also located at clearly recognizable focal positions.

12 Claims, 11 Drawing Sheets

FUNDUS EXAMINATION DEVICE CAPABLE OF AIDING IN GAZE FIXATION AND IMAGE FOCUSING

FIELD OF THE INVENTION

The present invention relates to an examination device applied to a fundus camera for split image focusing and aiding in gaze fixation; and more particularly to a fundus examination device that has gaze-fixation images and a split image screen located at different focal position corresponding to a human eye curvature. Therefore, when a split image focusing is completed, the gaze-fixation images are also located at clearly recognizable focal positions.

BACKGROUND OF THE INVENTION

A fundus camera is a camera particularly used for capturing images of inner eye and retina. Compared to other objects in photographing, the fundus does not give light itself. Light of different types projected onto an eye in a natural condition can illuminate the fundus but is not intense enough for observing the fundus or taking a picture thereof. Besides, light tends to reflect from the cornea to interfere with the observation of the fundus.

Therefore, the fundus camera must include an illuminating system capable of illuminating the fundus with a considerably intense light as well as an observing and imaging system that is free from any influence of the intense reflected light from the cornea on a film. Further, to distinguish the position of the macular or the optic disc from other areas in the captured eye image, fixation points are provided in the fundus camera, so that an examinee can turn his or her eye to a particular angle by gazing on some specific fixation point.

Please refer to FIG. 1. The gaze fixation system adopted by the conventional fundus camera mainly includes a liquid crystal display (LCD) 101, on which lightened spots 102 are provided at different positions. In using the LCD gaze fixation system, an examinee is caused to turn his or her eye and gaze on the lightened spots 102 on the LCD 101. Please refer to FIG. 2. The fundus camera using the conventional LCD gaze fixation system has an optical path design generally divided into an LCD display system 10, a light source projecting system 11, an optical camera system 12, an image displaying and monitoring system 13, and a positioning optical path system 14.

The LCD display system 10 includes an LCD display 101, a condenser lens 103 and a beam splitter 104. The light source projecting system 11 includes a photographing light source 111, a condenser lens 112, a ring-shaped slit plate 113, a relay lens 114 and a perforated mirror 115. The optical camera system 12 includes an ocular lens 121, a focusing lens 122, a magnifier 123 and a film 124. The image displaying and monitoring system 13 includes a beam-bending lens 131, a field lens 132, a mirror 133, a relay lens 134, a converter tube 135 and a monitor 136. The positioning optical path system 14 includes a semi-lens 141, a relay lens 142, a mirror 143, a light guide 144 and a light source 145.

Since the above optical path systems are independent from one another, they respectively require an independent optical path space. As a result, the fundus camera requires increased manufacturing cost. Further, the LCD for aiding gaze fixation does not include any optical path design related to a split image focusing screen. Therefore, an examiner could not quickly and precisely focus the image in the process of image focusing adjustment for individual eye diopter. However, the addition of a split image focusing system to the LCD display system would inevitably involve in the complicated problem of coordination with other optical path systems.

In view that there are still many improvements that must be made to the conventional fundus camera adopting the LCD for aiding in gaze fixation, it is tried by the inventor to develop an improved fundus examination device capable of aiding in gaze-fixation and image focusing.

SUMMARY OF THE INVENTION

A primary object of the present invention is to provide a fundus examination device capable of aiding an examinee in turning eye to gaze-fixation images, so that an examiner can conveniently focus the examination device on the fundus to capture different images thereof. In the fundus examination device, gaze fixation means and split image focusing means are integrated into a focusing zone, on which the examinee gazes, while the gaze-fixation images and a split image screen are located at different focusing positions corresponding to the examinee's eye curvature. Therefore, when a split image focusing is completed, the gaze-fixation images are also located at clearly recognizable focal positions, allowing the examinee to easily see the gaze-fixation images to ensure upgraded examination effect.

Another object of the present invention is to provide a fundus examination device capable of aiding in gaze fixation and image focusing, which allows an examiner to make split image focusing adjustment according to individual eye diopter, and allows different gaze fixation targets to be independently controlled to light or extinguish according to different requirements in a fundus examination, so that an examinee can turn his or her eye to a particular angle in response to a showed gaze fixation target.

A further object of the present invention is to provide a fundus examination device capable of aiding in gaze fixation and image focusing, which includes a gaze fixation device using an invisible light and intermittently lightened gaze-fixation images to build an examination condition having a high contrast between a black background and intermittently lightened spots, so that an examinee's eye is not stimulated by light and can more easily and comfortably gaze on the gaze-fixation images.

To achieve the above and other objects, the fundus examination device capable of aiding in gaze fixation and image focusing according to the present invention includes a light projecting device, an illuminating system, an imaging system, and a focusing and gaze-fixation device. The light projecting device projects an examination light to illuminate an examinee's fundus of eye. The illuminating system transmits the examination light to the examinee's eye and receives the examinee's fundus image. The imaging system is connected with the illuminating system for showing the fundus image. The focusing and gaze-fixation device is located in the illuminating system and includes a focus mask formed in a focusing zone, on which the examinee's eye gazes.

On the focus mask, there are provided a split image screen, a light-penetrable structure surrounding the split image screen, and at least one gaze fixation device. The gaze fixation device each forms a gaze-fixation image at a focusing position within the focusing zone, such that the split image screen and the gaze-fixation image are located at different focal positions corresponding to the examinee's eye curvature.

In a preferred embodiment of the present invention, the light-penetrable structure is configured as a curved structure to provide different focusing positions corresponding to the examinee's eye curvature; and the gaze fixation device each includes a light-emitting unit embedded in the curved structure for directly forming the gaze-fixation image at one corresponding focusing position.

In another preferred embodiment of the present invention, the light-penetrable structure is raised from the focus mask to form a stage structure higher than the split image screen; and the gaze fixation device each includes a light-emitting unit embedded in the stage structure for directly forming the gaze-fixation image at the corresponding focusing position.

In a further preferred embodiment of the present invention, the light-penetrable structure has a plurality of holes formed thereon, and the gaze fixation device each includes a lens fitted in one of the holes and a light-emitting unit arranged behind the lens. Therefore, light emitted by each light-emitting unit passes through the corresponding lens to indirectly show the gaze-fixation image at the examinee's eye focusing position.

In a still further preferred embodiment of the present invention, a reflecting surface capable of changing light's path is provided on the light-penetrable structure, and the gaze fixation device each includes a lens located in a light path of the reflecting surface and a light-emitting unit located behind the lens, so that light emitted by each light-emitting unit passes through the corresponding lens and is then reflected from the reflecting surface to indirectly show the gaze-fixation image at the focusing position within the focusing zone. And, the lens each is perpendicularly mounted to the light-penetrable structure and the reflecting surface is a 45-degree sloping surface with respect to the light-penetrable structure.

In the above-described four preferred embodiments, the light-emitting units can be light-emitting diodes, lamp tubes, light bulbs or optical fibers for projecting light. Further, the light-emitting units may be in the form of geometrical shapes, characters, figures, letters, symbols, patterns or any combination thereof.

Moreover, the light projecting device for the present invention consists of a visible light emitter and an invisible light emitter; and the imaging system includes a movable focusing lens, which and the split image screen cooperate with each other to together form a split image focusing means for selectively adjusting the focusing position to a position corresponding to the split image screen.

During a fundus examination using the present invention, the invisible light emitter is first used along with the movable focusing lens in an alignment procedure for focusing and gaze fixation, and the visible light emitter is then used in a photographing procedure for directly capturing the fundus image.

Further, in an operable embodiment, the fundus examination device has four gaze fixation devices, such that the gaze-fixation images formed by the four gaze fixation devices are separately located at an upper front, a lower front, a front left and a front right side of the split image screen.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
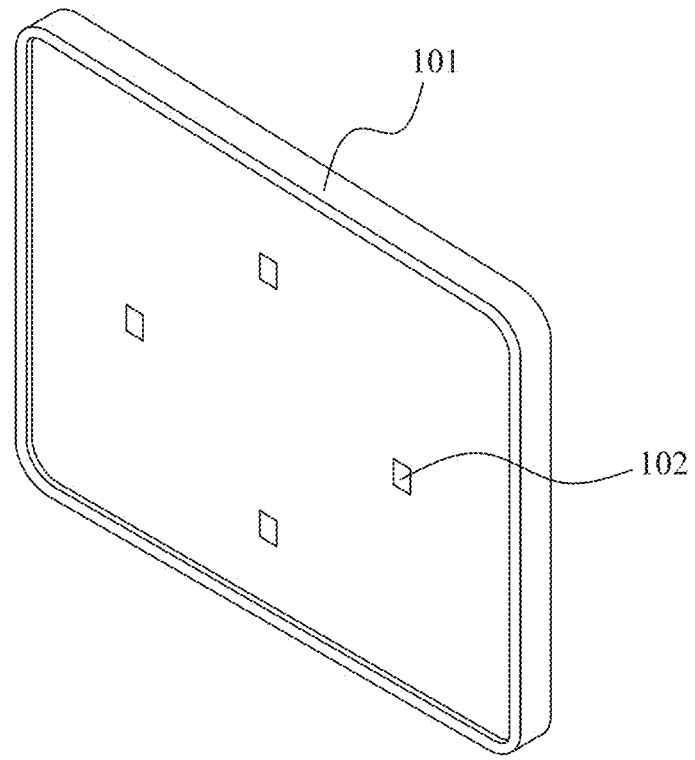
FIG. 1 is a perspective view of an LED display with fixation points conventionally employed in fundus examination.
Figure 2:
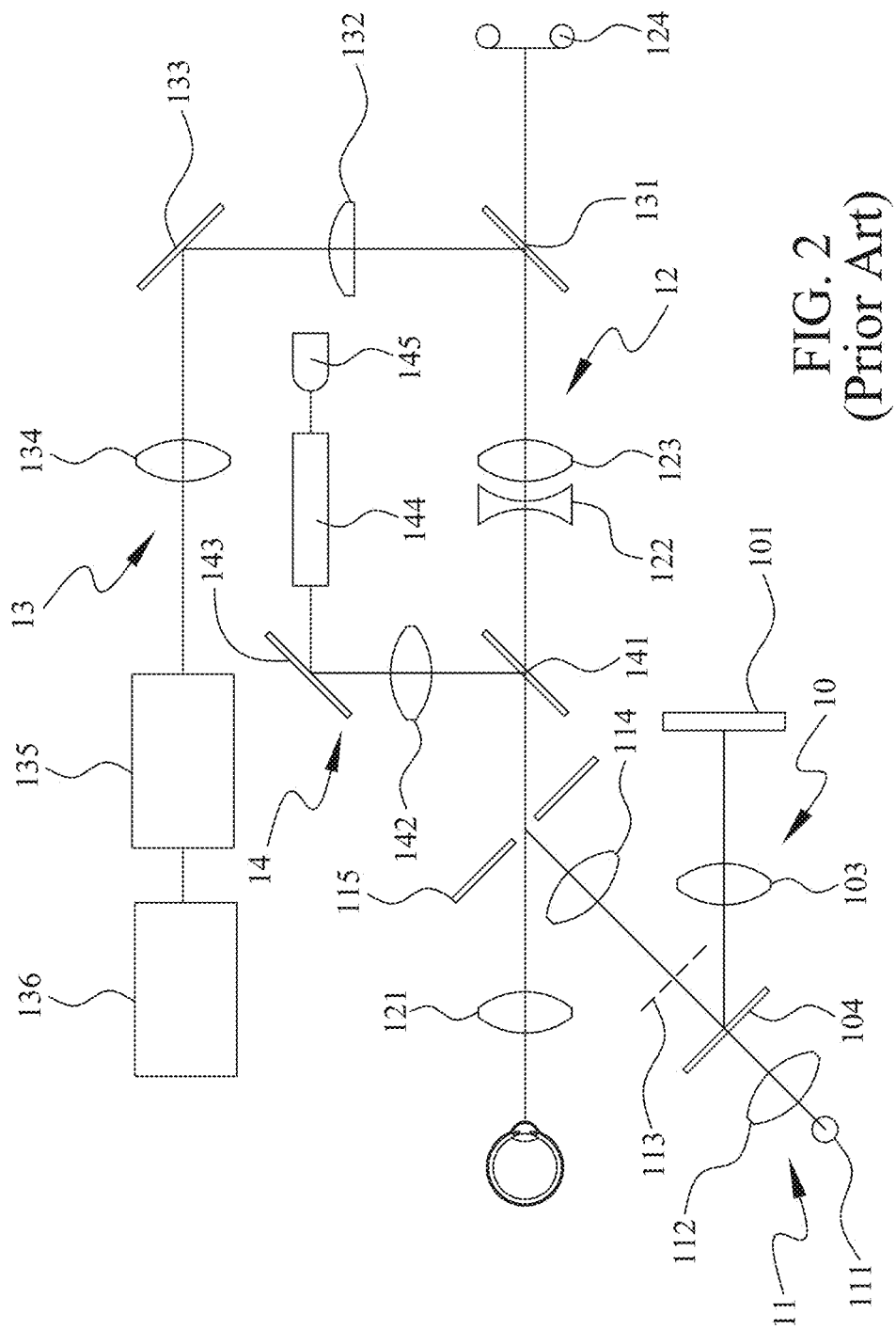
FIG. 2 is an optical path system diagram for a conventional fundus examination system employing the LED display of FIG. 1.

The present invention will now be described with some preferred embodiments thereof and with reference to the accompanying drawings. For the purpose of easy to understand, elements that are the same in the preferred embodiments are denoted by the same reference numerals.

To facilitate clear description of the technical features of the present invention, terms appeared in the specification are first defined as below. Unless otherwise specified, the term "system" mentioned herein means an assembly of lens, prisms, mirrors, lightproof plates and other various units that are needed to transmit light between an examinee's eye, an illuminating device and a display to form an image; and the term "optical path" mentioned herein means a path in any system along which light is transmitted from a light projection start point, such as the illuminating device and the examinee's eye, to a light projection end point, such as the examinee's eye and the display.

Figure 3:
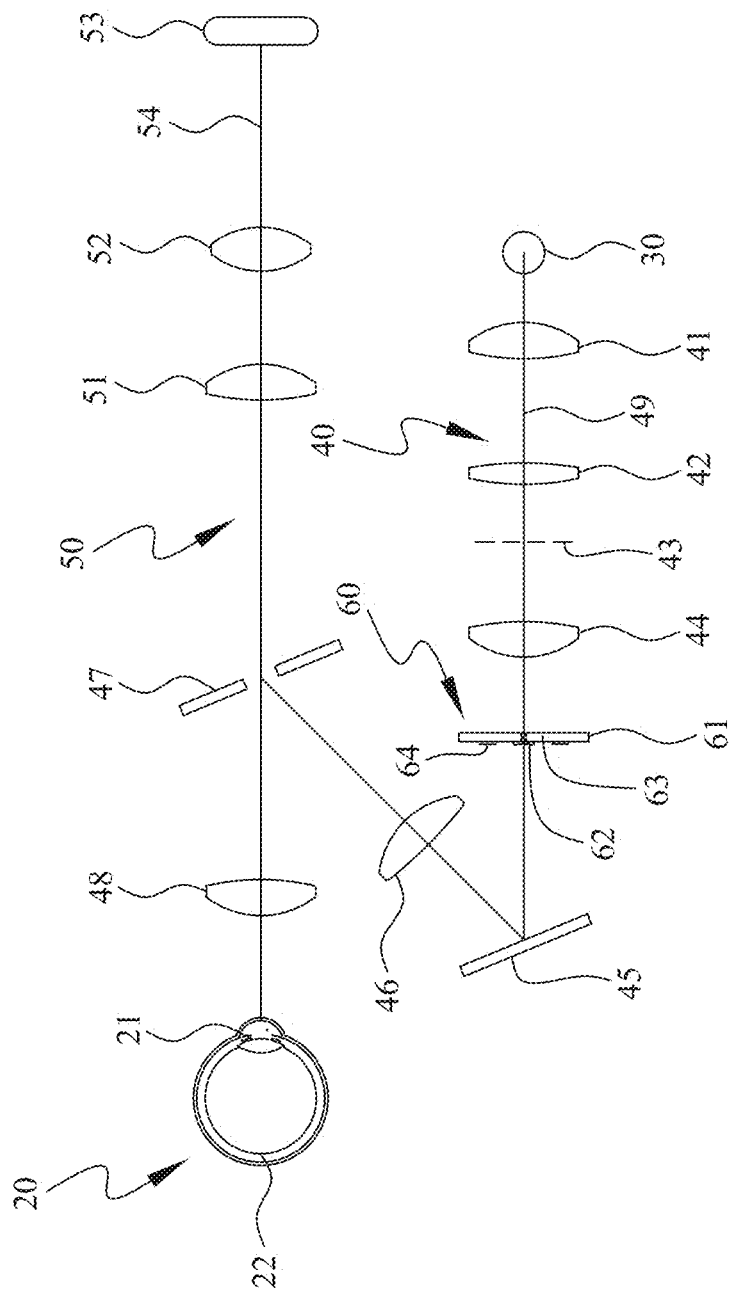
FIG. 3 is an optical path system diagram for a fundus examination device according to the present invention.

Please refer to FIG. 3. The present invention is a fundus examination device capable of aiding in gaze fixation and image focusing mainly used to capture the image of an examinee's fundus 22 via the examinee's pupil 21 of eye 20. In an operable preferred embodiment of the present invention, the fundus examination device includes a light projecting device 30, a condenser lens 41, a first lens 42, a ring-shaped slit plate 43, a second lens 44, a mirror 45, a third lens 46, a perforated mirror 47, an ocular lens 48, a relay lens 51, a focusing lens 52, and a display 53 based on CMOS (complementary metal-oxide-semiconductor) sensor technology.

The light projecting device 30 consists of a visible light emitter and an invisible light emitter for projecting an examination light to illuminate the fundus 22 of the examinee's eye 20. The condenser lens 41, the first lens 42, the ring-shaped slit plate 43, the second lens 44, the mirror 45, the third lens 46, the perforated mirror 47 and the ocular lens 48 together constitute an illuminating system 40 for transmitting the examination light to the examinee's eye 20 and receiving an image of the examinee's fundus 22. On the other hand, the ocular lens 48, the perforated mirror 47, the relay lens 51, the focusing lens 52 and the display 53 together constitute an imaging system 50 for displaying the fundus image.

In the illuminating system 40, the light projecting device 30 projects the examination light onto the condenser lens 41 and the first lens 42 to thereby form an image on the ring-shaped slit plate 43. The examination light then passes the ring-shaped slit plate 43 and is projected onto the mirror 45 via the second lens 44. The mirror 45 redirects the examination light to the third lens 46, via which the examination light is projected onto the perforated mirror 47. Finally, the perforated mirror 47 reflects the examination light onto the examinee's eye 20 to illuminate the examinee's fundus 22. Therefore, a photographing optical path 49 from the light projecting device 30 to the fundus 22 is formed in the illuminating system 40. In the above design, the light projecting device 30, the ring-shaped slit plate 43 and the examinee's pupil 21 of eye 20 are conjugate planes, allowing an examiner to precisely control an aperture size of a fundus camera, which uses the fundus examination device of the present invention, for forming an image on the examinee's pupil 21 without being affected by any size difference or position deviation of the light emitters in the light projecting device 30.

In the imaging system 50, the ocular lens 48 receives the examinee's fundus image. The fundus image and light reflected from the examinee's eye pass through a perforation on the perforated mirror 47, the relay lens 51 and the focusing lens 52 to finally show on the display 53. Therefore, an image-displaying optical path 54 from the examinee's eye 20 to the display 53 is formed in the imaging system 50.

Figure 4:
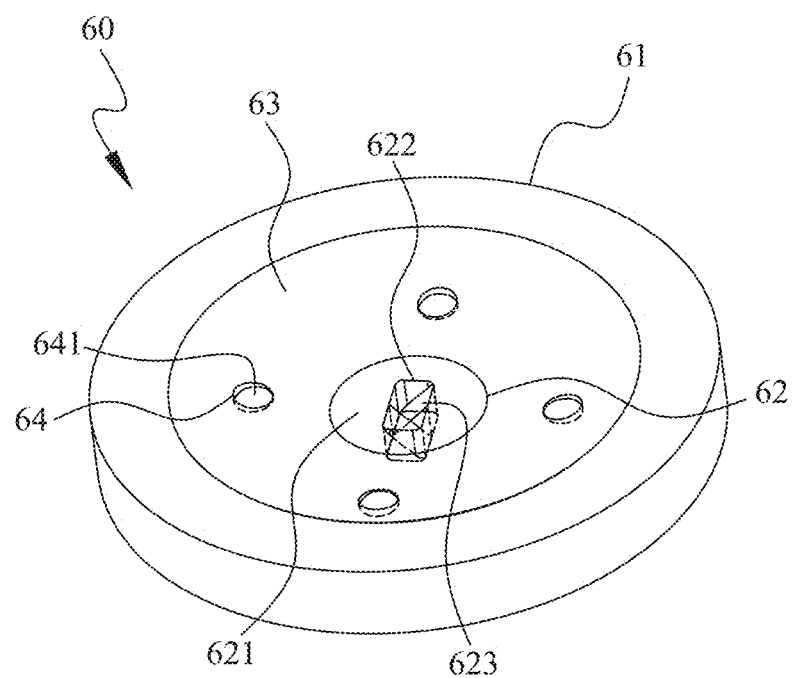
FIG. 4 is a perspective view of a focusing and gaze-fixation device for the fundus examination device according to a first preferred embodiment of the present invention.
Figure 5:
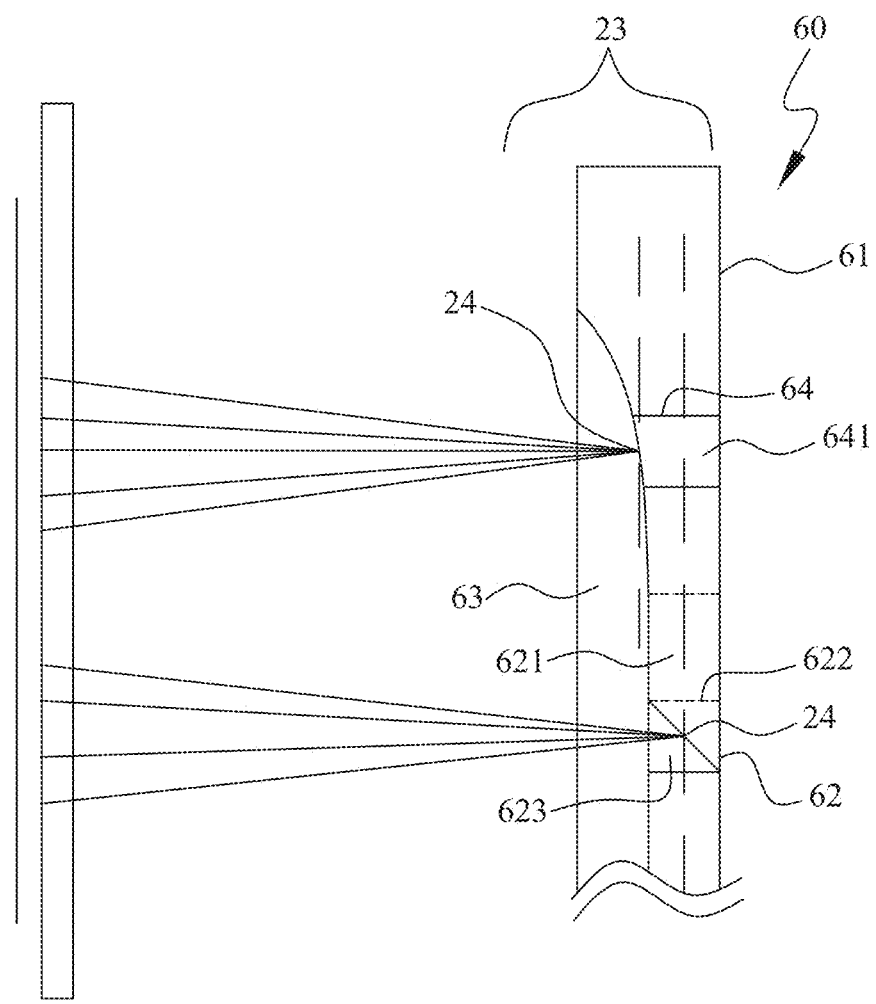
FIG. 5 shows how the focusing and gaze-fixation device of FIG. 4 focuses.

In the present invention, a focusing and gaze-fixation device 60 is further provided between the mirror 45 and the second lens 44 in the illuminating system 40. Please refer to FIGS. 4 and 5. In a first preferred embodiment of the present invention, the focusing and gaze-fixation device 60 includes a focus mask 61 formed within a focusing zone 23, on which the examinee's eye 20 focuses.

The focus mask 61 in the first preferred embodiment includes a split image screen 62, a light-penetrable structure 63 surrounding the split image screen 62, and four gaze fixation devices 64. The split image screen 62 and the focusing lens 52 cooperate with each other to together form a split image focusing means capable of changing focal position. With the focusing lens 52, it is able to selectively adjust a focusing position 24 of the examinee's eye 20 to a position corresponding to the split image screen 62. The split image screen 62 includes a light blocking plate 621 of a predetermined size, on which a light-transmissible slit 622 is provided; and two facing prisms 623 are arranged in front of the slit 622. The examination light passes through the slit 622 and is changed in direction by the prisms 623 to form two rectangular image parts on the display 53 for indicating whether an image is in focus.

The light-penetrable structure 63 is located around the light blocking plate 621 to allow the examination light projected by the visible light emitter and the invisible light emitter to pass therethrough.

The four gaze fixation devices 64 are arranged on the light-penetrable structure 63 to locate at an upper, a lower, a left and a right side of the split image screen 62, and can respectively form a gaze-fixation image at one focusing position 24 of the examinee's eye 20 in the focusing zone 23, so that the split image screen 62 and the gaze-fixation images are separately located at different focal positions corresponding to the examinee's eye curvature. Further, due to a contrast between the gaze-fixation images and the examination light, the gaze-fixation images form gaze fixation targets, allowing the examinee to turn the eye 20 to a particular angle in response to the gaze fixation target that is showed on the light-penetrable structure 63.

In the first preferred embodiment of the present invention, the light-penetrable structure 63 is configured as a curved structure to provide different focusing positions 24 corresponding to the examinee's eye curvature; and the gaze fixation devices 64 respectively include a light-emitting unit 641 embedded in the light-penetrable structure 63. The light-emitting units 641 can be light-emitting diodes (LEDs), and the gaze-fixation images are respectively a round light spot. With these arrangements, the light-emitting units 641, at the time the image focusing is completed via the split image screen 62, will be directly located at the focusing positions 24 of the examinee's eye 20 to respectively directly project a clearly visible gaze-fixation image.

When using the present invention to conduct a fundus examination, first use the invisible light emitter and the movable focusing lens 52 in an alignment procedure for focusing and gaze fixation, and then, use the gaze fixation devices 64 and the visible light emitter in a photographing procedure for capturing fundus images, so that the examiner can obtain fundus images captured from different angles.

In the present invention, an invisible-light background and a plurality of intermittently lightened light-emitting units 641 are used in the fundus examination, and the gaze fixation devices 64 can be independently controlled to light or extinguish the light-emitting units 641 thereof, allowing the examinee to more easily and comfortably gaze on the gaze fixation targets in the high contrast between the black background and the light spots.

Figure 6:
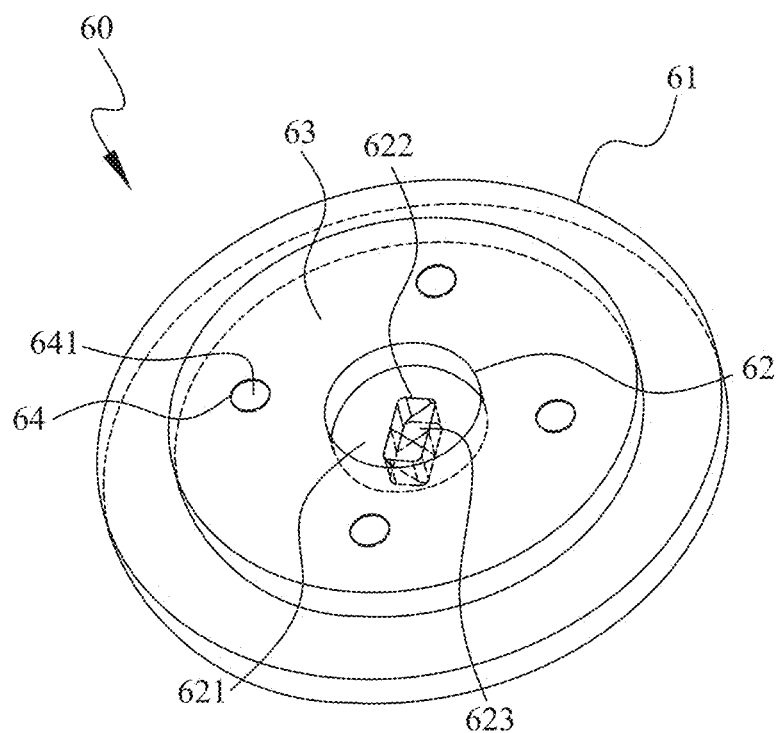
FIG. 6 is a perspective view of the focusing and gaze-fixation device for the fundus examination device according to a second preferred embodiment of the present invention.
Figure 7:
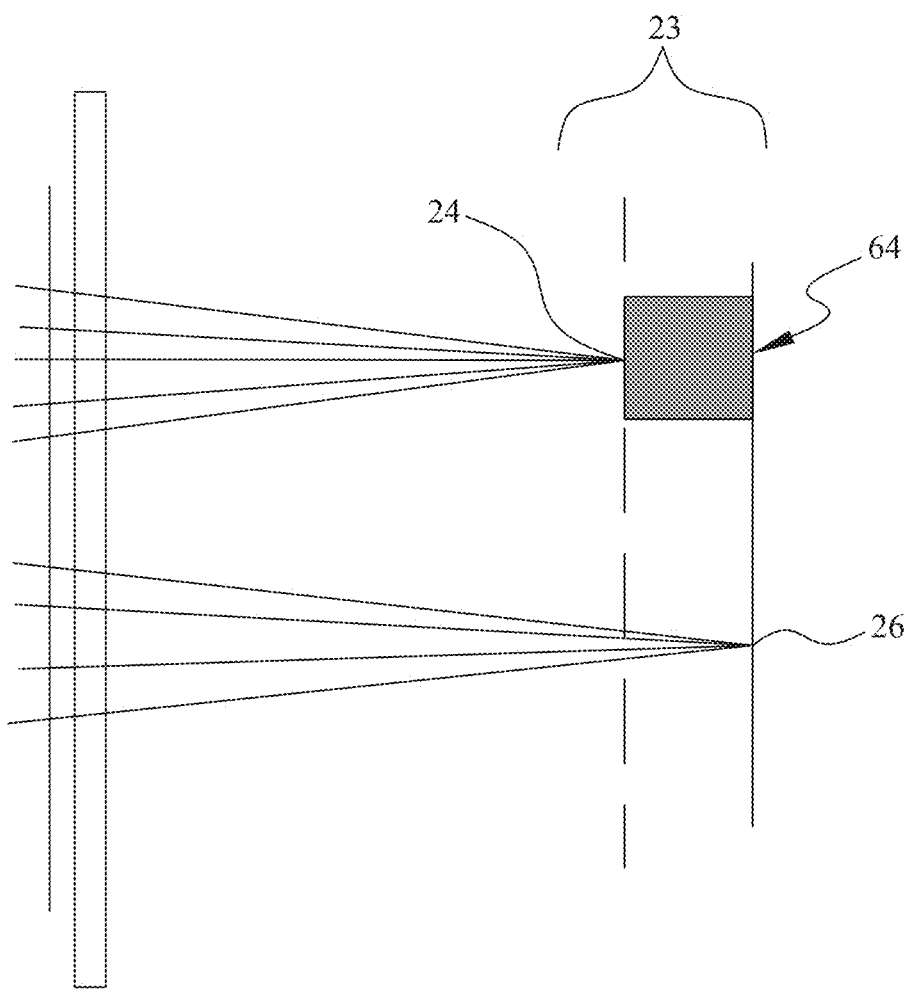
FIG. 7 shows how the focusing and gaze-fixation device of FIG. 6 focuses.

Please refer to FIGS. 6 and 7. In the focusing and gaze-fixation device 60 according to a second preferred embodiment of the present invention, the light-penetrable structure 63 is raised from the focus mask 61 to form a stage structure higher than the split image screen 62. The gaze fixation devices 64 respectively include a light-emitting unit 641 embedded in the stage structure, and the light-emitting units 641 are located corresponding to the examinee's eye focusing positions 24 for directly forming a gaze-fixation image at each of the focusing positions 24.

Figure 8:
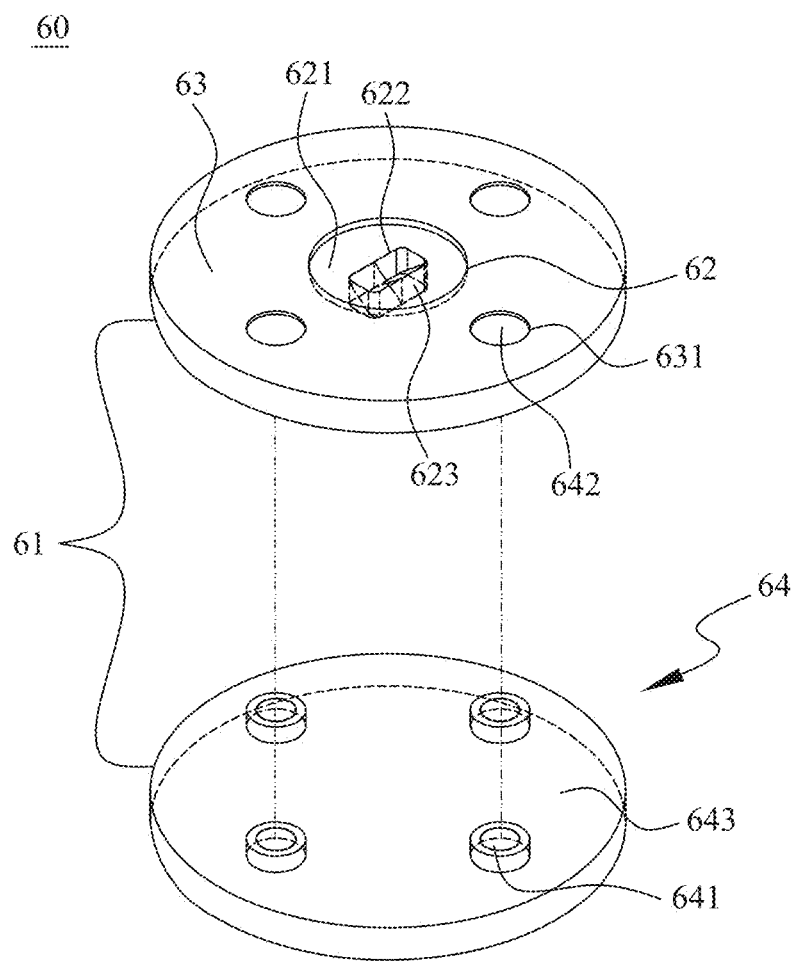
FIG. 8 is an exploded perspective view of the focusing and gaze-fixation device for the fundus examination device according to a third preferred embodiment of the present invention.
Figure 9:
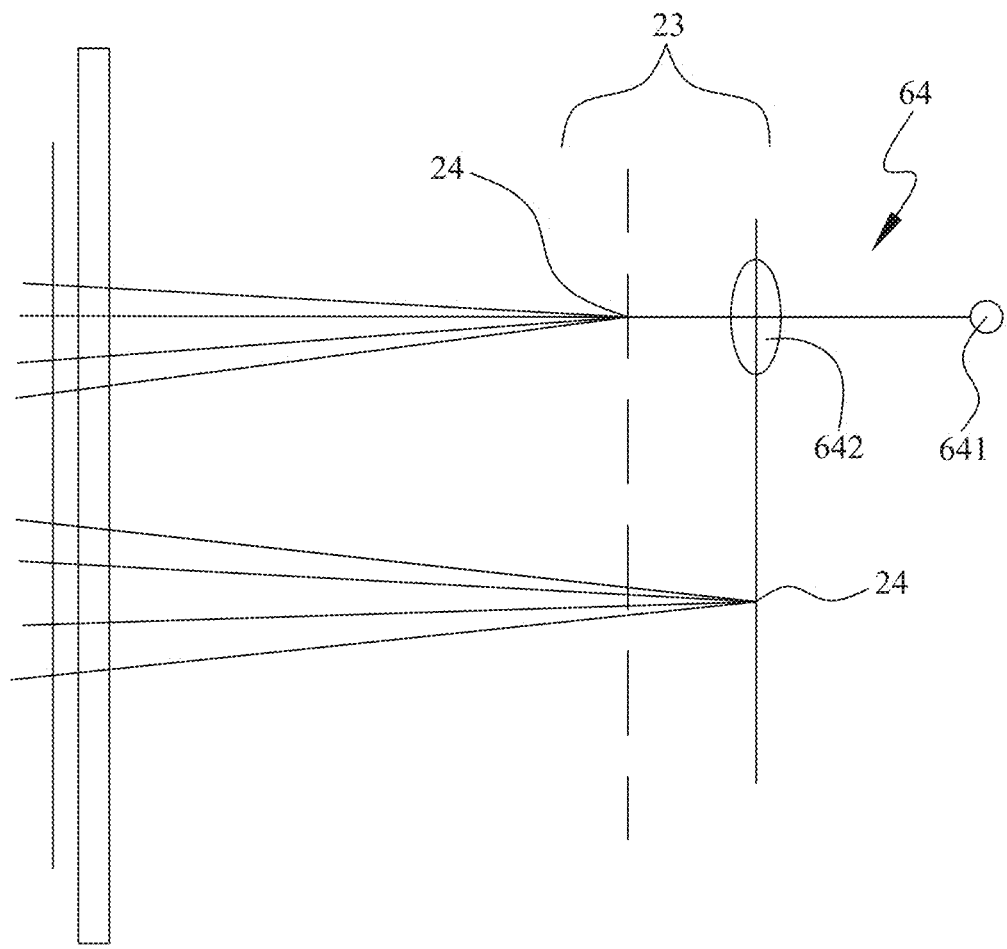
FIG. 9 shows how the focusing and gaze-fixation device of FIG. 8 focuses.

Please refer to FIGS. 8 and 9. In the focusing and gaze-fixation device 60 according to a third preferred embodiment of the present invention, the light-penetrable structure 63 has a plurality of holes 631 formed thereon, and the gaze fixation devices 64 respectively include a lens 642 fitted in a corresponding one of the holes 631 and a light-emitting unit 641 arranged behind each of the lenses 642. It is noted the light-emitting units 641 of the gaze fixation devices 64 are assembled to a mating light-penetrable structure 643. In the third preferred embodiment, light emitted by the light-emitting units 641 of the gaze fixation devices 64 passes through the corresponding lenses 642 to indirectly show the gaze-fixation images at the examinee's eye focusing positions 24, which are located ahead the split image screen 62.

Figure 10:
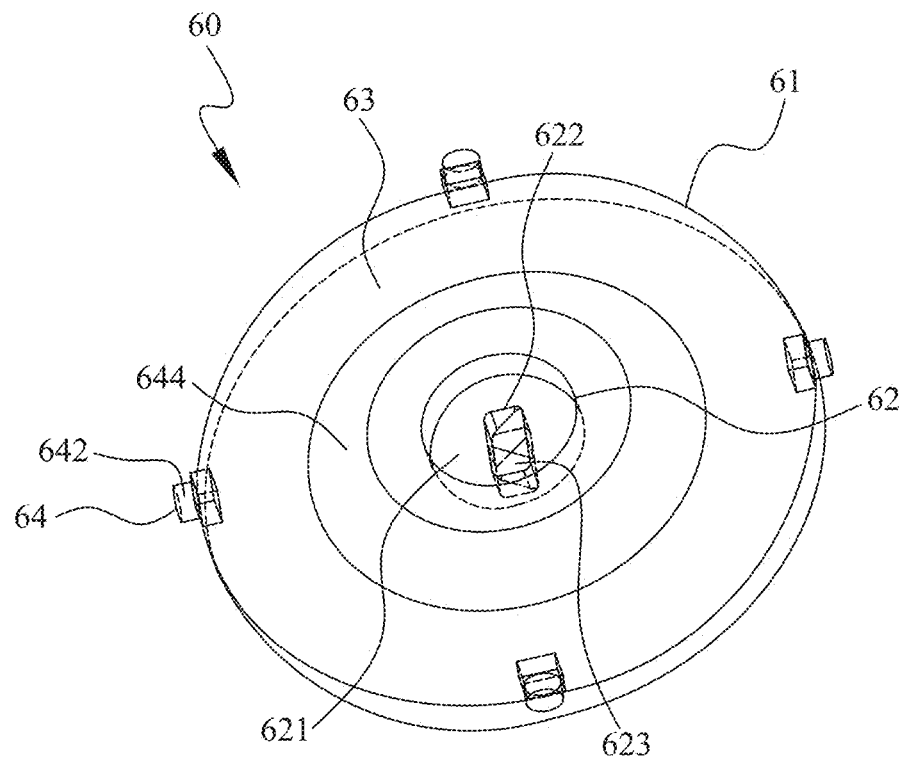
FIG. 10 is an exploded perspective view of the focusing and gaze-fixation device for the fundus examination device according to a fourth preferred embodiment of the present invention.
Figure 11:
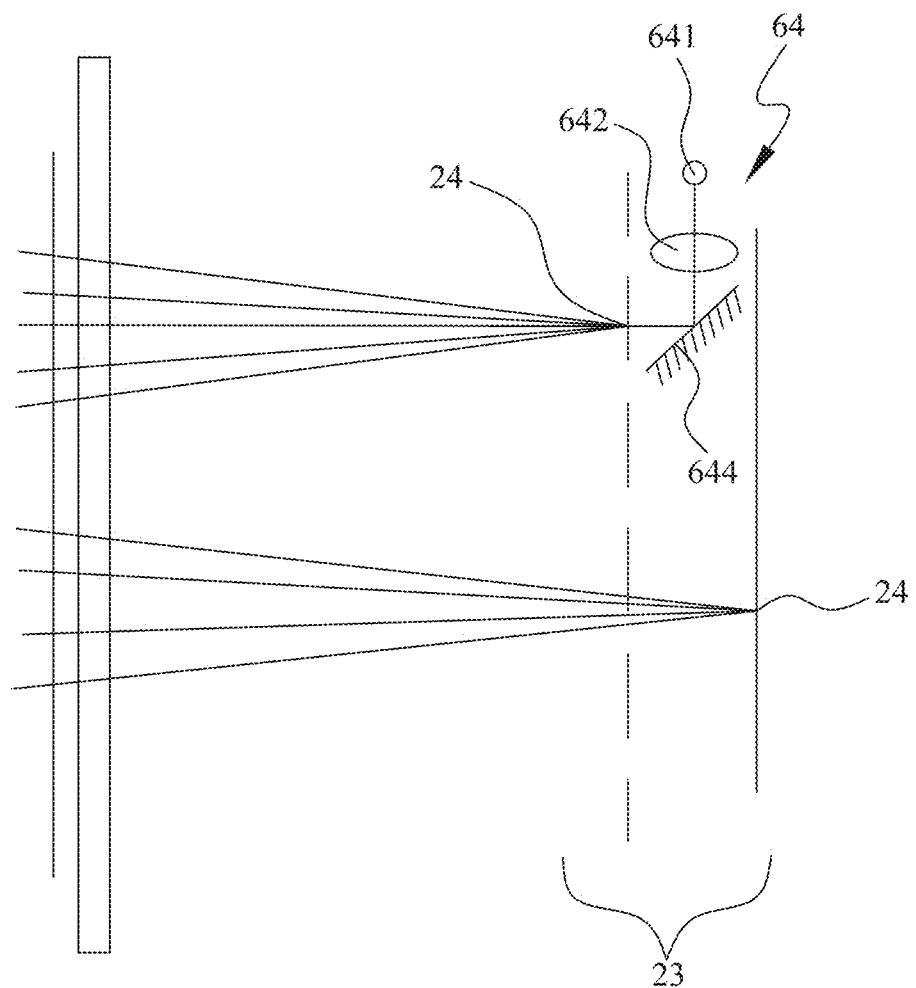
FIG. 11 shows how the focusing and gaze-fixation device of FIG. 10 focuses.

Please refer to FIGS. 10 and 11. In the focusing and gaze-fixation device 60 according to a fourth preferred embodiment of the present invention, a reflecting surface 644 capable of changing light's path is provided on the light-penetrable structure 63, and the gaze fixation devices 64 respectively include a lens 642 located in a light path of the reflecting surface 644 and a light-emitting unit 641 located behind the lens 642. The lenses 642 are perpendicularly mounted to an outer peripheral edge of the light-penetrable structure 63, and the reflecting surface 644 is a 45-degree sloping surface with respect to the light-penetrable structure 63. The light projected by the light-emitting units 641 passing through the lenses 642 and reflected from the reflecting surface 644 indirectly forms the gaze-fixation images at the examinee's eye focusing positions 24 within the focusing zone 23.

The positions of the gaze-fixation images and the type of the light-emitting units 641 described in the first to the fourth preferred embodiment are only illustrative and not intended to limit the design of the light-emitting units 641. That is, the light-emitting units 641 can be otherwise configured as lamp tubes, light bulbs or optical fibers according to examination requirements. Further, in addition to the round shape as shown in the illustrated drawings, the light-emitting units 641 may also be in the form of other geometrical shapes, characters, figures, letters, symbols, patterns or any combination thereof.

In summary, according to the present invention, means for gaze fixation and split image focusing are integrated into the examinee's eye focusing zone, and the faze-fixation images and the split image screen are located at positions corresponding to a human eye's curvature. Therefore, at the time the split image focusing is completed, the gaze-fixation images are also located at the clearly recognizable focal positions, allowing the examinee to easily see the gaze-fixation images to ensure upgraded examination effect. Moreover, the present invention allows the examiner to make split image focusing adjustment according to individual eye diopter, and allows different gaze fixation targets to be independently controlled to light or extinguish according to different requirements in an eye examination, so that an examinee can turn his or her eye to a particular angle in response to a showed gaze fixation target. In addition, the present invention uses invisible light and intermittently lightened gaze-fixation images, so that the high contrast between the black background and the flashing spots enables the examinee to more easily and comfortably gaze on the fixation points without being stimulated by light.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A fundus examination device capable of aiding in gaze fixation and image focusing, comprising:
    a light projecting device for projecting an examination light to illuminate an examinee's fundus of eye, the light projecting device consisting of a visible light emitter and an invisible light emitter, wherein the invisible light emitter is first used in an alignment procedure for focusing and gaze fixation, and the visible light emitter is then used in a photographing procedure for capturing the fundus image;
    an illuminating system for transmitting the examination light to the examinee's eye and receiving an image of the examinee's fundus;
    an imaging system connected with the illuminating system for showing the fundus image, the imaging system including a movable focusing lens; and
    a focusing and gaze-fixation device located in the illuminating system and including a focus mask formed within a focusing zone on which the examinee's eye focuses; the focus mask including a split image screen, a light-penetrable structure surrounding the split image screen, and at least one gaze fixation device; and the gaze fixation device each forming a gaze-fixation image at a focusing position within the focusing zone, such that the split image screen and the gaze-fixation image are located at different focal positions corresponding to the examinee's eye curvature;
    wherein the movable focusing lens and the split image screen cooperate with each other together to form a split image focusing means for selectively adjusting the focusing position to a position corresponding to the split image screen and the gaze-fixation image.

2. The fundus examination device as claimed in claim 1, wherein the light-penetrable structure is configured as a curved structure to provide different focusing positions corresponding to the examinee's eye curvature; and the gaze fixation device each including a light-emitting unit embedded in the curved structure for directly forming the gaze-fixation image at one corresponding focusing position.

3. The fundus examination device as claimed in claim 2, wherein the light-penetrable structure is raised from the focus mask to form a stage structure higher than the split image screen; and the gaze fixation device each including a light-emitting unit embedded in the stage structure for directly forming the gaze-fixation image at the corresponding focusing position.

4. The fundus examination device as claimed in claim 3, wherein the light-emitting unit each is selected from the group consisting of a light-emitting diode (LED), a lamp tube, a light bulb, and an optical fiber.

5. The fundus examination device as claimed in claim 2, wherein the light-emitting unit each is selected from the group consisting of a light-emitting diode (LED), a lamp tube, a light bulb, and an optical fiber.

6. The fundus examination device as claimed in claim 1, wherein the light-penetrable structure has a plurality of holes formed thereon, and the gaze fixation device each includes a lens fitted in one of the holes and a light-emitting unit arranged behind the lens; whereby, light emitted by each light-emitting unit passes through the corresponding lens to indirectly show the gaze-fixation image at the examinee's eye focusing position.

7. The fundus examination device as claimed in claim 6, wherein the light-emitting unit each is selected from the group consisting of a light-emitting diode (LED), a lamp tube, a light bulb, and an optical fiber.

8. The fundus examination device as claimed in claim 1, wherein a reflecting surface capable of changing light's path is provided on the light-penetrable structure, and the gaze fixation device each includes a lens located in a light path of the reflecting surface and a light-emitting unit located behind the lens, so that light emitted by each light-emitting unit passes through the corresponding lens and is reflected from the reflecting surface to indirectly show the gaze-fixation image at the focusing position within the focusing zone.

9. The fundus examination device as claimed in claim 8, wherein the reflecting surface is a 45-degree sloping surface with respect to the light-penetrable structure and the lens each is perpendicularly mounted to the light-penetrable structure.

10. The fundus examination device as claimed in claim 8, wherein the light-emitting unit each is selected from the group consisting of a light-emitting diode (LED), a lamp tube, a light bulb, and an optical fiber.

11. The fundus examination device as claimed in claim 1, wherein the gaze-fixation image each is in a form selected from the group consisting of a geometrical shape, a character, a figure, a letter, a symbol, a pattern, and any combination thereof.

12. The fundus examination device as claimed in claim 1, wherein four gaze fixation devices are provided on the focus mask, such that the gaze-fixation images formed by the four gaze fixation devices are separately located at an upper front, a lower front, a front left and a front right side of the split image screen.

* * * * *